(12) United States Patent
Raja et al.

(10) Patent No.: US 9,962,376 B2
(45) Date of Patent: May 8, 2018

(54) METHODS AND OPHTHALMIC DEVICES USED IN THE TREATMENT OF OCULAR ALLERGIES

(75) Inventors: Ranganath R. Raja, Jacksonville, FL (US); Shivkumar Mahadevan, Orange Park, FL (US); Azaam Alti, Jacksonville, FL (US); Frank F. Molock, Orange Park, FL (US); Brain Pall, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 1295 days.

(21) Appl. No.: 11/686,979

(22) Filed: Mar. 16, 2007

(65) Prior Publication Data

US 2008/0085922 A1    Apr. 10, 2008

Related U.S. Application Data

(60) Provisional application No. 60/848,332, filed on Sep. 29, 2006.

(51) Int. Cl.
| | |
|---|---|
| *A61K 31/4535* | (2006.01) |
| *A61K 9/00* | (2006.01) |
| *G02B 1/04* | (2006.01) |
| *A61L 12/04* | (2006.01) |

(52) U.S. Cl.
CPC ........ *A61K 31/4535* (2013.01); *A61K 9/0051* (2013.01); *A61L 12/04* (2013.01); *G02B 1/043* (2013.01)

(58) Field of Classification Search
None
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,113,224 A | 9/1978 | Clark |
| 4,197,266 A | 4/1980 | Clark |
| 4,495,313 A | 1/1985 | Larsen |
| 4,680,336 A | 7/1987 | Larsen |
| 4,691,820 A | 9/1987 | Martinez |
| 4,889,664 A | 12/1989 | Kindt Larsen |
| 5,364,884 A | 11/1994 | Varma et al. |
| 5,467,868 A | 11/1995 | Abrams |
| 5,488,815 A | 2/1996 | Abrams |
| 5,577,367 A | 11/1996 | Abrams |
| 5,607,688 A | 3/1997 | Cejkova et al. |
| 5,696,686 A | 12/1997 | Sanka |
| 5,704,468 A | 1/1998 | Lust |
| 5,710,302 A | 1/1998 | Kunzler |
| 5,760,100 A | 6/1998 | Nicolson |
| 5,760,100 B1 | 6/1998 | Nicolson |
| 5,776,999 A | 7/1998 | Nicolson |
| 5,776,999 B1 | 7/1998 | Nicolson |
| 5,789,461 A | 8/1998 | Nicolson |
| 5,789,461 B1 | 8/1998 | Nicolson |
| 5,823,327 A | 10/1998 | Wu |
| 5,849,811 A | 12/1998 | Nicolson |
| 5,849,811 B1 | 12/1998 | Nicolson |
| 5,965,631 A | 10/1999 | Nicolson |
| 5,998,498 A | 12/1999 | Vanderlaan |
| 6,018,931 A | 2/2000 | Byram |
| 6,050,398 A | 4/2000 | Wilde |
| 6,087,415 A | 7/2000 | Vanderlaan |
| D435,966 S | 1/2001 | Duis |
| 6,395,756 B2 | 5/2002 | Trimming |
| 6,624,193 B1 | 9/2003 | Naka |
| 6,713,080 B1 | 3/2004 | Aiache et al. |
| 6,767,097 B2 | 7/2004 | Streibig |
| 6,774,137 B2 | 8/2004 | Adam |
| 6,776,982 B2 | 8/2004 | Kis |
| 6,777,429 B1 | 8/2004 | Adam |
| 6,822,016 B2 | 11/2004 | McCabe |
| 7,172,286 B2 | 2/2007 | Streibig |
| 7,722,808 B2 * | 5/2010 | Matsuzawa .......... A45C 11/005 206/5.1 |
| 2001/0006968 A1 * | 7/2001 | Trimming et al. ...... 514/254.07 |
| 2002/0133889 A1 | 9/2002 | Molock |
| 2003/0000028 A1 | 1/2003 | Molock |
| 2003/0203001 A1 | 10/2003 | Schultz |
| 2004/0034042 A1 | 2/2004 | Tsuji |
| 2006/0008506 A1 | 1/2006 | Cipriano De Sousa |
| 2006/0100408 A1 | 5/2006 | Powell |
| 2006/0177483 A1 | 8/2006 | Byrne |
| 2006/0187410 A1 | 8/2006 | Sato |
| 2006/0216328 A1 | 9/2006 | Kis |

FOREIGN PATENT DOCUMENTS

| | | |
|---|---|---|
| DE | 4337492 A1 | 5/1995 |
| EP | 406161 A2 | 1/1991 |
| EP | 0420598 | 4/1991 |
| EP | 1611877 | 1/2006 |
| EP | 1617277 | 1/2006 |
| JP | 2001-505792 A | 5/2001 |
| JP | 2003-26565 A | 7/2001 |

(Continued)

OTHER PUBLICATIONS

Karlgard et al (Int J Pharmaceut 257:141-151, 2003.*
Schock et al (J Ocular Pharmacol Therapeut 19(1):75-81, 2003).*
Abelson et al (Pediatric Allergy and Immunology 15:551-557, 2004—Abstract only).*
David A. Leigh et al. Angew. Chem Int. Ed., 2001, 40, No. 8, pp. 1538-1542.
Jean-Claude Chambron et al. Pure & appl. Chen., 1990, vol. 62, No. 6, pp. 1027-1034.
American Journal of Ophthalmology vol. 130, No. 6, pp. 717-732.
Karlgard, C.C. et al., "In vitro uptake and release studies of ocular pharmaceutical agents by silicon-containing and p-HEMA hydrogel contact lens materials", International Journal of Pharmaceutics, vol. 257, No. 102, May 12, 2003, pp. 141-151.
U.S. Appl. No. 60/783,557, filed Mar. 17, 2006.
PCT International Search Report for Application No. PCT/US2007/064147 dated Jan. 2, 2008.

(Continued)

*Primary Examiner* — Craig D Ricci (57) ABSTRACT

Ophthalmic devices and methods of treating allergic conjunctivitis are disclosed herein.

6 Claims, 1 Drawing Sheet

(56) References Cited

FOREIGN PATENT DOCUMENTS

| | | |
|---|---|---|
| JP | 2002-510627 A | 4/2002 |
| JP | 2004-175770 A | 6/2004 |
| JP | 2004-315365 A | 11/2004 |
| JP | 2005-529122 A | 9/2005 |
| JP | 2006515321 | 5/2006 |
| WO | WO 1994021698 A1 | 9/1994 |
| WO | WO 99/36055 | 7/1999 |
| WO | WO 99/51230 | 10/1999 |
| WO | WO 2002057837 A2 | 7/2002 |
| WO | WO 2003057837 A2 | 7/2003 |
| WO | WO 2004-090613 A | 10/2004 |
| WO | WO 2005027954 | 3/2005 |
| WO | 2006039558 A2 | 4/2006 |
| WO | WO 06/084275 | 8/2006 |
| WO | WO 2007109523 A | 9/2007 |

OTHER PUBLICATIONS

Alvarez-Lorenzo, Carmen, Soft Contact Lenses Capable of Sustained Delivery of Timolol. Journal Pharm. Sci., Oct. 2002, pp. 2182-2192, vol. 91, No. 10.

Chambron et al. Interlacing Molecular Threads on Transition Metals (1990) Pure & Appl. Chem., vol. 62, No. 6, pp. 1027-1034.

Ehlers, William H. et al., Therapeutic Contact Lenses, Opth Clinics of North America, Mar. 1996, pp. 87-100, vol. 9, No. 1.

Graus et al. Keterolac in the Analgesia for Photoablative Refractive Procedures for Myopia. Investigative Opthalmology & Visual Science (1995) vol. 36, No. 5 pp. 3280-267.

Hehl, E.M., Improved Penetration of Aminoglycosides and Fluoroquinolones into the Aqueous Humour of Patients by Means of Acuvue Contact Lenses. Eur. J. Clin Pharmocol. (1999) vol. 55 pp. 317-323.

Hiratani, H. et al. Timolol Uptake and Release by Inprinted Soft Contact Lenses Made of N,N-Diethylacrylamide and Methacrylic Acid. Journal of Controlled Release (2002) vol. 83, pp. 223-230.

Karlgard, et al. In Vitro Uptake and Release Studies of Ocular Pharmaceutical Agents by Silicon-Containing and p-HEMA Hydrogel Contact Lens Material. Int'l Journal of Pharm. (2003) vol. 257, pp. 141-151.

Krejci et al. Intraocular Penetration of Cysteine from Hydrophilic Gel Contact Lenses Through the Intact, Epithelium-Denuded and Lime-Burned Cornea. Ophthal. Res. (1976) 8 pp. 93-99.

Lesher et al. Continuous Drug Delivery Through the Use of Disposable Contact Lenses, (1993), vol. 70, No. 12, pp. 1012-1018.

Leigh et al. Benzylic Imine Catenates: Readily Accessible Octahedral Analogues of the Sauvage Catenates (2001) vol. 40, No. 8 pp. 1538-1543.

Momose et al. Adsorption of Levocabastine Eye Drops by Soft Contact Lenses and its Effects in Rabbit Eyes (1997) CLAO Journal vol. 23, No. 2 pp. 96-99.

Praus et al. Elution and Intraocular Penetration of the Ophthalmic Drugs of Different Molecular Weights from the Hydrophilic Contact Lenses Through the Intact and Injured Cornea. Acta Universitatis Carol. Med. (1977) vol. 23, No. ½, pp. 3-10.

Temel A. et al. Effect of the Application of Acetazolamide Soaked Contact Lenses on Intraocular Pressure of Rabbits. Documenta Opthalmologica. (1992) vol. 82 pp. 323-329.

Tian, X. et al. Studies on the Uptake and release of Fluoroquinolones by Disposable Contact Lenses. CLAO Journal (2001), vol. 27, No. 4, pp. 216-220.

Tian, X. et al. Disposable 1-Day Acuvue® Contact Lenses for the Delivery of Lomefloxacin to Rabbits' Eyes. CLAO Journal (2001) vol. 27, No. 4 pp. 212-215.

Waltman, S.R. et al. Use of Hydrophilic Contact Lenses to Increase Ocular Penetration of Topical Drugs. Investigative Ophth. (1970) vol. 9 pp. 250-255.

Winder, A.F. et al. Drug Release and Lens Spoilation (1975) vol. 68, No. 1 pp. 57-59.

A Glimpse Into the Future. Int'l Journal of Pharm. Compounding, May/Jun.(1998) vol. 2, No. 3 pp. 203-204.

Soluri et al, Delivery of Ketotifen Fumarate by Commercial Contact Lens Materials, Optometry and Vision Science, vol. 89, No. 8, pp. 1140-1149, (2012).

UNC, Sterile Compounding, Ophthalmics, The Pharmaceutics and Compounding Laboratory, 2012.

Clin Exp Optom 2000; 83*5):257-270, p. 262, table 5.

* cited by examiner

METHODS AND OPHTHALMIC DEVICES USED IN THE TREATMENT OF OCULAR ALLERGIES

RELATED APPLICATIONS

This application claims priority from a non-provisional filing, U.S. patent application Ser. No. 60/848,332 which was filed on Sep. 29, 2006.

FIELD OF THE INVENTION

This invention related to devices and treatments for allergic conjunctivitis.

BACKGROUND

Allergic conjunctivitis is a disease of the eye that affects millions of people. The symptoms of this disease include itchiness, tearing, and swelling of the eyes. Sometimes this disease is seasonally associated with the spring and summer hay fever seasons, but many people experience symptoms of this disease throughout the year. The symptoms of allergic conjunctivitis are caused and mediated by the binding of histamine to its receptor. Antihistamines are a class of pharmaceutical agent known to either or both suppress the release of histamine from associated mast cells and prevent the binding of histamine to its associated receptors. These agents have been used to treat the symptoms of allergic conjunctivitis and one such agent is ketotifen fumarate. Topical solutions of ketotifen fumarate are currently sold in the United States. The concentration ketotifen in of the U.S. approved ketotifen fumarate formulation is 0.025% (0.25 mg/mL). At that concentration, the recommended dosing regimen is twice daily. It is known that the recommended dosing can be reduced if the amount of ketotifen fumarate is increased, but it is also known that higher concentrations of ketotifen fumarate sting and burn upon initial administration to the eye.

Further it is known that they symptoms of allergic conjunctivitis have a greater impact on the wearers of contact lenses. Many contact lens wearers stop using their lenses during the spring and summer hay fever seasons and other peak allergen seasons. Contact lens wearers can administer topical ketotifen solutions to reduce the symptoms of allergic conjunctivitis. However, if the inconvenience of carrying a bottle of solution can be avoided, it would be beneficial. In addition, since it is known that higher concentrations of the ketotifen fumarate can cause stinging and burning, it would be beneficial if the symptoms of allergic conjunctivitis were alleviated by administering an amount of ketotifen fumarate to patients that did not cause stinging in a dose that lasts longer than 6 hours. These benefits are provided by the following invention.

DETAILED DESCRIPTION OF THE INVENTION

This invention includes an ophthalmic device comprising about a minimum effective amount of an anti-allergic agent. As used herein "anti-allergic agent" refers to chemical substances that alleviate the symptoms of allergic conjunctivitis. While not wishing to be bound by any particular mechanism of action, anti-allergic agents include but are not limited to chemical substances that inhibit the release of histamine, that block the binding of histamine to its receptors, inhibit mast cell production. Additional anti-allergic agents include but are not limited to decongestants, non-steroidal anti-inflammatory compound, and steroidal compounds. Particularly, examples of anti-allergic agents include but are not limited to acetmetacin, acrivastine, aldosterone, antazoline, astemizole, azatadine, azelastine, beclometasone, betamethasone, bromfenac, buclizine, carprofen, cetirizine, chloropyriline, chlorpheniramine, clemastine, cromolyn, cyclizine, cyproheptadine, dexamethasone, diazoline, diclofenac, diphenhydramine, ebastine, emedastine, epinastine, etodolac, fenbufen, fenoprofen, fexofenadine, fludrocortisone, flurbiprofen, flurometalone, hydroxyzine, ibuprofen, indometacin, ketoprofen, ketorolac tromethamine, ketotifen, levocabastine, levoceterizine, lodoxamide, loratadine, loteprednol, loxoprofen, medrysone, mepivacaine, mequitazine, methdilazine, methapyrilene, nabumetone, naphazoline, naproxen, nedocromil, norastemizole, norebastine, olopatadine, phenidamine, phenylephrine, oxatamide, oxymetazoline, pemirolast, pheniramine, picumast, prednisilone, promethazine, rimexalone, repirinast, sulindac, suprofen, tetrahydozoline, terfenadine, tiaprofenic acid, tometim, tranilast, triamcinolone, trimeprazine, triprolidine, and pharmaceutically acceptable salts and mixtures thereof. Preferred anti-allergic agent include acrivatine, antazoline, astemizole, azatadine, azelastine, clemastine, cyproheptadine, ebastine, emedastine, fexofenadine, hydroxyzine, ketotifen, levocabastine, levoceterizine, mequitazine, methdialazine, methapyrilene, norastemizole, norebastine, picumast, promethazine, terfenadine, trimeprazine, triprolidine, and pharmaceutically acceptable salts and mixtures thereof. The class of substances known as antihistamines are the particularly preferred anti-allergic agents The particularly preferred antihistamines include, azelastine, epinastine, ketotifen, ketotifen fumarate, nor-ketotifen fumarate, olopatadine and mixtures thereof. More particularly preferred antihistamines include ketotifen, its pharmaceutically acceptable salts and mixtures thereof.

The term "minimum effective amount" refers to the weight of anti-allergic agent contained in an ophthalmic device prior to its use by a patient wherein such minimum effective amount alleviates the symptoms of allergic conjunctivitis. The minimum effective amount may vary depending upon the efficacy of a particular anti-allergic agent. For example, if the anti-allergic agent is ketotifen fumarate, the minimum effective amount is between greater than about 9 μg and about less than 90 μg, more particularly between about 40 μg and greater than about 9 μg, most preferably about for 20 μg. It is preferred that minimum effective amount of anti-allergic agent other than ketotifen fumarate is an amount that exhibits an efficacy equivalent to or more efficacious greater than about 9 μg and about less than 90 μg, more particularly between about 40 μg and about 9 μg of ketotifen fumarate.

It is preferred that the minimum effective amount of anti-allergic agent alleviates the symptoms of allergic conjunctivitis for between about 5 minutes, and about 24 hours from insertion of the ophthalmic device into the eye of a user, more preferably between about 5 minutes and about 16 hours, most preferably between about 5 minutes and about 12 hours.

As used herein, "ophthalmic device" refers to an object that resides in or on the eye. These devices can provide optical correction or may be cosmetic. Ophthalmic devices include but are not limited to soft contact lenses, intraocular lenses, overlay lenses, ocular inserts, punctual plugs, and optical inserts. The preferred ophthalmic devices of the invention are soft contact lenses made from silicone elastomers or hydrogels, which include but are not limited to silicone hydrogels, and fluorohydrogels and excludes ophthalmic devices that contain phosphate group-containing methacrylates (i.e. $CH_2=C(CH_3)-C(O)-(CH_2)_n-O-P(O)(OH)_2$, where n is 1-4; $CH_2C=C(CH_3)-C(O)-(CH_2)_2-O-P(O)(OH)-O-(CH_2)_2-O-C(O)-C(CH_3)=CH_2$) or pre-polymers as such defined by US Pat. Application Publication No. US 2006/0100408. Soft contact lens formulations are disclosed in U.S. Pat. No. 5,710,302, WO 9421698, EP 406161, JP 2000016905, U.S. Pat. Nos. 5,998,498, 6,087,415, 5,760,100, 5,776, 999, 5,789,461, 5,849,811, and 5,965,631. The foregoing references are hereby incorporated by reference in their entirety. The particularly preferred ophthalmic devices of the inventions are prepared from formulations known by the United States Approved Names of acofilcon A, alofilcon A, alphafilcon A, amifilcon A, astifilcon A, atalafilcon A, balafilcon A, bisfilcon A, bufilcon A, comfilcon, crofilcon A, cyclofilcon A, darfilcon A, deltafilcon A, deltafilcon B, dimefilcon A, drooxifilcon A, epsifilcon A, esterifilcon A, etafilcon A, focofilcon A, galyfilcon A, genfilcon A, govafilcon A, hefilcon A, hefilcon B, hefilcon D, hilafilcon A, hilafilcon B, hioxifilcon B, hioxifilcon C, hixoifilcon A, hydrofilcon A, lenefilcon A, licryfilcon A, licryfilcon B, lidofilcon A, lidofilcon B, lotrafilcon A, lotrafilcon B, mafilcon A, mesifilcon A, methafilcon B, mipafilcon A, nelfilcon A, netrafilcon A, ocufilcon A, ocufilcon B, ocufilcon C, ocufilcon D, ocufilcon E, ofilcon A, omafilcon A, oxyfilcon A, pentafilcon A, perfilcon A, pevafilcon A, phemfilcon A, polymacon, senofilcon A, silafilcon A, siloxyfilcon A, tefilcon A, tetrafilcon A, trifilcon A, vasurfilcon, vifilcon, and xylofilcon A. More particularly preferred ophthalmic devices of the invention are genfilcon A, lenefilcon A, comfilcon, lotrafilcon A, lotraifilcon B, and balafilcon A. More preferred lenses include comfilcon, etafilcon A, galyfilcon A, senofilcon A, nelfilcon A, hilafilcon, tetrafilcon A, vasurfilcon, vifilcon, and polymacon. The most preferred lenses include etafilcon A.

Further the invention includes a method of alleviating the symptoms of allergic conjunctivitis comprising administering to a patient an ophthalmic device comprising about a minimum effective amount of an anti-allergic agent. The terms ophthalmic device, minimum effective amount and anti-allergic agent all have their aforementioned meanings and preferred ranges. As used herein, the term "administering" means placing the ophthalmic device of the invention onto the surface of the eye, or in the eye, of a patient. If the device is in contact with the anterior surface of the patient's eye, such as a soft contact lens, it is preferred that the ophthalmic device remain in contact with that surface for between about 5 minutes, and about 24 hours from insertion of the ophthalmic device into the eye of a user, more preferably between about 5 minutes and about 16 hours, more preferably between about 5 minutes and about 12 hours, most preferably between about 5 minutes and greater than about 12 hours. If the ophthalmic device is contained within the eye or on the ocular adnexa, such as a punctual plug or an ocular insert, it is preferred that the device remain in contact with the eye for at least 24 hours.

Still further the invention includes a method of making an ophthalmic device comprising about a minimum effective amount of an anti-allergic agent comprising the step of treating an ophthalmic device with a solution comprising said anti-allergic agent, wherein the amount of said anti-allergic agent in said solution exceeds the minimum effective amount. It is preferred that the minimum effective amount is exceeded by between about 1.0% and about 1000%, in a volume of solution that is between about 500 µL and about 5000 µL preferably between about 50% and about 500%, in a volume of solution that is between about 500 µL and about 3000 µL most preferably about 50% in a volume of solution that is about 1000 µL.

As used herein treating means physical methods of contacting the solution containing an anti-allergic agent and the ophthalmic device. Preferably treating refers to physical methods of contacting the anti-allergic agent with the ophthalmic devices prior to selling or otherwise delivering the ophthalmic devices to a patient. The ophthalmic devices may be treated with the anti-allergic agent anytime after they are polymerized. Polymerization refers to the process in which components of an ophthalmic device including but not limited to monomers, pre-polymers, diluents, catalysts, initiators, tints, UV blockers, antibacterial agents, polymerization inhibitors, and the like are reacted by thermal, chemical, and light initiated curing techniques to produce a formed polymer. The preferred methods of polymerization are the light initiated techniques disclosed in U.S. Pat. No. 6,822,016 which is hereby incorporated by reference in its entirety. It is preferred that the polymerized ophthalmic devices be treated with anti-allergic agent at temperature of greater than about 50° C. For example in some processes to manufacture contact lenses, an un-polymerized, or partially polymerized formulation is placed between two mold halves, spincasted, or static casted and polymerized. See, U.S. Pat. Nos. 4,495,313; 4,680,336; 4,889,664, 3,408.429; 3,660,545; 4,113,224; and 4,197,266, all of which are incorporated by reference in their entirety. In the case of hydrogels, the ophthalmic device formulation is a hardened disc that is subjected to a number of different processing steps including treating the polymerized ophthalmic device with liquids (such as water, inorganic salts, or organic solutions) to swell, or otherwise equilibrate this polymerized ophthalmic device prior to enclosing the polymerized ophthalmic device in its final packaging. Polymerized ophthalmic devices that have not been swelled or otherwise equilibrated are known as un-hydrated polymerized ophthalmic devices. The addition of the anti-allergic agent to any of the liquids of this "swelling" or "equilibrating" step at room temperature or below is considered "treating" the lenses with anti-allergic agent as contemplated by this invention. In addition, the polymerized un-hydrated ophthalmic devices may be heated above room temperature with the anti-allergic agent during swelling or equilibrating steps. The preferred temperature range is from about 50° C. for about 15 minutes to about sterilization conditions as described below, more preferably from about 50° C. to about 85° C. for about 5 minutes.

Examples of blister packages and sterilization techniques are disclosed in the following references which are hereby incorporated by reference in their entirety, U.S. Pat. Nos. D435,966; 4,691,820; 5,467,868; 5,704,468; 5,823,327; 6,050,398, 5,696,686; 6,018,931; 5,577,367; and 5,488,815. This portion of the manufacturing process presents another method of treating the ophthalmic devices with anti-allergic agent, namely adding anti-allergic agents to a solution prior to sealing the package, and subsequently sterilizing the package. This is the preferred method of treating ophthalmic devices with anti-allergic agents.

Sterilization can take place at different temperatures and periods of time. The preferred sterilization conditions range from about 100° C. for about 8 hours to about 150° C. for about 0.5 minute. More preferred sterilization conditions range from about 115° C. for about 2.5 hours to about 130° C. for about 5.0 minutes. The most preferred sterilization conditions are about 124° C. for about 18 minutes.

The "solutions" that are used in methods of this invention may be water-based solutions. Typical solutions include, without limitation, saline solutions, other buffered solutions, and deionized water. The preferred aqueous solution is deionized water or saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Preferably, the solution is a borate buffered or phosphate buffered saline solution or deionized water. The particularly preferred solution contains about 500 ppm to about 18,500 ppm sodium borate, most particularly preferred about 1000 ppm of sodium borate.

If the anti-allergic agents are subject to oxidative degradation, agents that stabilize solutions containing such anti-allergic agents may be added. Such "oxidative stabilization agents" include but are not limited to chelants such as EDTA, Dequest, Desferal, silica, chitin derivatives such as chitosan, cellulose and its derivatives, and N,N,N',N',N",N"-hexa(2-pyridyl)-1,3,5-tris(aminomethyl)benzene, and certain macrocyclic ligands such as crown ethers, ligand containing knots and catenands. See, David A. Leigh et al *Angew. Chem Int. Ed.*, 2001, 40, No. 8, pgs. 1538-1542 and Jean-Claude Chambron et al. *Pure & Appl. Chem.*, 1990, Vol. 62, No. 6, pgs. 1027-1034. Oxidative stabilization agents may include other compounds that inhibit oxidations such as those selected from the group consisting of 2,2',2", 6,6',6"-Hexa-(1,1-dimethylethyl)4,4',4"-[(2,4,6-trimethyl-1,3,5-benzenetriyl)-trismethylene]-triphenol (Irganox 1330), 1,3,5tris[3,5-di(1,1-dimethylethyl)4-hydroxybenzyl]-1H, 3H,5H-1,3,5-triazine-2,4,6-trione, pentaerythrityl tetrakis[3-[3,5-di(1,1-dimethylethyl)-4-hydroxyphenyl]-propionate], octadecyl-3-[3,5-di(1,1-dimethylethyl)-4-hydroxyphenyl]-propionate, tris[2,4-di(1,1-dimethylethyl)-phenyl]-phosphite, 2,2'-di(octadecyloxy)-5,5'-spirobi(1,3,2-dioxaphosphorinane), dioctadecyl disulphide, didodecyl-3,3'-thiodipropionate, dioctadecyl-3,3'-thiodipropionate, butylhydroxytoluene, ethylene bis[3,3-di[3-(1,1-dimethylethyl)-4-hydroxyphenyl]butyrate] and mixtures thereof. The preferred oxidative stabilization agents are diethylenetriaminepentaacetic acid ("DTPA"), or salts of DTPA such as $CaNa_3DTPA$, $ZnNa_3DTPA$, and $Ca_2DTPA$. See, U.S. patent application No. 60/783,557 filed on, Mar. 17, 2006, entitled "Methods for Stabilizing Oxidatively Unstable Pharmaceutical Compositions" and its corresponding non-provisional filing which are hereby incorporated by reference in their entirety. Therefore, the invention includes a method of preventing oxidation of an ophthalmic device comprising an anti-allergic agent, wherein the method includes treating said ophthalmic device with a solution comprising an oxidative stabilization agent. It is preferred that at the concentration of oxidative stabilization agents in the solution be from about 2.5 µmoles/liter to about, 5000 µmoles/liter more preferably from about 20 µmoles/liter to about 1000 µmoles/liter, more preferably from about 100 µmoles/liter to about 1000 µmoles/liter, most preferably from about 100 µmoles/liter to about 500 µmoles/liter.

Yet still further the invention includes an ophthalmic device comprising about a localized amount of an anti-allergic agent. As used herein the terms anti-allergic agent and ophthalmic device have their afore mentioned preferred identities and preferred ranges.

As used herein, the term "localized amount" refers to an amount of anti-allergic agent that located in discrete portions of the ophthalmic device. For example, the localized amount may be on the front or back surface (using those terms as applied to contact lenses) of the device, or in any other area or surface. It is preferred that the localized amount remain in contact with the conjunctiva of the eye when placed in the eye of a user. It is preferred that the localized amount of anti-allergic agent is between about 1 µg and about 200 µg, preferably between about 1 µg and about 90 µg, more preferably between about 1 µg and about 50 µg, most preferably between about 2 µg and about 20 µg. The anti-effective agent may be adding to a discrete area of the device by including the anti-allergic agent in coatings or pigments that may be added to the devices. See, U.S. Pat. Nos. 7,172,286; and 6,767,097, WO 02/057837, WO 03/057837 U.S. Pat. App. Nos. US 2002/0133889, and US 2003/0000028 coatings and pigments that may be applied to ophthalmic devices as well methods of applying the same to such devices Yet further still the invention includes a method of alleviating the symptoms of allergic conjunctivitis comprising administering to a patient an ophthalmic device comprising about a localized amount of an anti-allergic agent. As used herein the terms anti-allergic agent, localized amount, and ophthalmic device have their afore mentioned preferred identities and preferred ranges.

Still further, the invention includes a method alleviating the symptoms of allergic conjunctivitis in a patient for an extended period of time, wherein said method comprises administering to the eye of said patient an administration system comprising said anti-allergic agent, wherein said administration system releases to said patient a dosing effective amount of an anti-allergic agent. The term anti-allergic agent has its aforementioned meaning. The "extended period of time" is from about 5 minutes to about greater than 24 hours depending upon the administration system. The term administration system refers to a physical object that contains an anti-allergic agent that releases the contained anti-allergic to the eye of a patient over time. The preferred administration systems are ophthalmic devices that are exposed to the anterior surface of the eye, in the eye, or on the ocular adnexa. Such preferred administrative systems include soft contact lenses, punctual plugs or ocular inserts, most particularly, the soft contact lenses of this invention. If the administration system is a soft contact lens the preferred extended period of time is greater than about 12 hours, more preferably between about 13 hours and about 24 hours, most preferably between about 13 hours and about 18 hours. If the administration system is a punctual plug or an ocular insert, the preferred period of time is greater than 24 hours. The term "administering" means placing said administration system on or in the eye of a patient. The term "releases" means separating the anti-allergic agent from its administration system so that said anti-allergic agent is available to eye of a patient. If the ophthalmic device is administered to the anterior surface of the eye, it is preferred that the administration system release between about 10% and about 90% of its contained anti-allergic agent between administering the device to the eye and about 60 minutes, more preferably between 10% and about 70% in about 30 minutes. If the administration system does not contact the exterior surface of the eye and is placed in another portion of the eye, it is preferred that such administration system release its contained anti-allergic agent over a period of time equal to or greater than 24 hours. The term "dosing effective amount" refers to an amount of anti-allergic agent sufficient to alleviate the symptoms of allergic conjunctivitis for an extended period of time. This amount may vary depending upon the potency of the anti-allergic agent. For example if the ophthalmic device contains ketotifen, the preferred dosage effective amount is between about less than 1 µg and about 20 µg. The preferred dosage effective amount is between about less than 1 µg and about 20 µg. It is preferred that the dosing effective amount of ketotifen released to the eye of a patient from about 1 minute to about 300 minutes. It is particularly preferred that between about 10% and about 75% of the ketotifen contained within the ophthalmic device is delivered to the eye of a patient within about 60 minutes.

In order to illustrate the invention the following examples are included. These examples do not limit the invention. They are meant only to suggest a method of practicing the invention. Those knowledgeable in contact lenses as well as other specialties may find other methods of practicing the invention. However, those methods are deemed to be within the scope of this invention.

EXAMPLES

Example 1

Preparation of Ophthalmic Devices Containing 10 µg and 25 µg of Ketotifen Fumarate To prepare 1000g of a 10 µg/mL ketotifen fumarate ("K-10:
1. 9.10 g of boric acid
2. 1.00 g of sodium borate decahydrate
3. 8.30 g of sodium chloride
4. 0.10 g of Ca2DTPA
5. 981.49 g of deionized water
6. 0.01 g of ketotifen fumarate The system is maintained at room temperature throughout the solution making process. All components 1-6 are added in any order and stirred using a magnetic or mechanical stirrer until the solution is homogeneous. Ketotifen fumarate is added last and the mixture is stirred for an additional 30 minutes or as long as it takes to make the solution homogeneous.

The procedure to prepare a 25 ug/mL ketotifen fumarate solution is identical to that described above, with the only exceptions being the amount of ketotifen fumarate (0.025 g instead of 0.010 g) and water (981.475 g instead of 981.49 g).

1-Day Acuvue® Brand Contact Lenses (etafilcon A) were removed from their packages and repackaged in glass vials containing 3.0 mL of the 10 µg/mL or the 25 µg/mL ketotifen fumarate solutions described above to produce K-Lens 10 and K-Lens 25 respectively. The vials were sealed with PTFE coated rubber stoppers and heated for 18 minutes at 124° C.

Example 2

Clinical Evaluation of Ophthalmic Devices of Example 1

This was a single-center double-masked, randomized, placebo controlled, clinical trial to assess the efficacy of the lenses of Example 1 in a conjunctivial allergen challenge (CAC Model ). See, Netland et al, Emedastine Ophthalmic Solution 0.05% Versus Levocabastine Ophthalmic Suspension 0.05% in the Treatment of Allergic Conjunctivitis Using the Conjunctival Allergen Challenge Model, *American Journal of Ophthalmology* VOL. 130, No. 6, page 717-723, 718 for a description of a positive test to a CAC challenge. At the first visit (Day—28±3), subjects underwent an allergen titration and a contact lens fitting. During the allergen titration, a CAC was performed bilaterally with animal (cat) allergens, grass, tree, or wood pollens. Beginning with the lowest dose, one drop (25 µL) of solubilized allergen was instilled into the conjunctival cul-de-sac bilaterally. If the subject failed to react within 10 minutes, increasing doses may have been instilled in both eyes at a minimum of ten minute intervals until a positive reaction was elicited. A positive CAC was defined as at least Grade 2.0+ redness in both eyes in 2 of the 3 vessel beds (conjunctival, ciliary, and episcleral), and 2.0+ inching in both eyes, within 10 minutes of receiving that dose of allergen. Subjects were then be given an approved OTC antiallergy eye drop after all CAC evaluations were completed to relieve any ocular itching or redness. Subjects were then fitted with placebo lenses. Lens fit was evaluated approximately 30 minutes after insertion. Subjects were then given a one week supply of placebo lenses with the instructions to use on a daily basis.

At the second visit (Study Day—14±3), subjects underwent an allergen titration with contact lenses. Subjects inserted a new set of placebo lenses in each eye. Subjects then underwent a CAC with one drop of allergen dilution one dose lower than previously determined at Visit 1 instilled into each eye. If after 10 minutes the subject failed to react positively to the allergen (≥Grade 2 redness and ≥Grade 2 itching OU in 2 of the 3 vessel beds), the subject was re-challenged with a higher dose. Subjects were then given another week supply of daily wear contact lenses.

At Visit 3 (Study Day—7±3), an allergen confirmation was done. This visit also served as an untreated comparison visit. Subjects inserted a new set of placebo lenses in each eye. Subjects then underwent CAC with one drop of allergen dose previously determined at Visit 2 to have induced an allergic response instilled into each eye. Subjects evaluated ocular itching prior to CAC challenge and 3, 5, and 7 minutes following the allergen instillation. Investigators evaluated conjunctival, episcleral and ciliary hyperemia, chemosis and mucous discharge prior to the CAC challenge and 7, 15 and 20 minutes following the allergen instillation. Tearing and lid swelling were evaluated by the subject prior to CAC challenge and at 7, 15 and 20 minutes post-challenge. Subjects were then given another week supply of daily wear contact lenses.

Visit 4 evaluated the effectiveness of K-Lens solution instilled 12 hours prior to CAC. Subjects were randomly assigned to one of five treatment groups: K-Lens 10/Placebo, K-Lens 25/Placebo, K-Lens 10/K-Lens 10, K-Lens 25/K-Lens 25, and Placebo/Placebo. For the contralateral eye subjects (K-Lens and placebo), the K-Lens was counterbalanced between the OD and OS eye. After inserting the assigned contact lens with the designated solution, subjects waited at the site for 30 minutes for a visual acuity examination, slit lamp biomicroscopy, and lens fit evaluation. Subjects were then allowed to leave the office with instructions to return 11 hours later. At 12 hours post lens insertion, subjects underwent CAC. Subjects evaluated ocular itching prior to CAC challenge and 3, 5, and 7 minutes following the allergen instillation. Investigators evaluated conjunctival, episcleral and ciliary hyperemia, chemosis, and mucous discharge prior to the CAC challenge and 7, 15 and 20 minutes following the allergen instillation. Tearing and lid swelling were evaluated by the subject prior to the CAC challenge and at 7, 15 and 20 minutes post-challenge. Subjects were then given another two week supply of daily wear contact lenses.

Visit 5 evaluated the effectiveness of K-Lens solution instilled 8 hours prior to CAC. Subjects received the contact lenses in the same solution that they received at Visit 4. After inserting the assigned contact lens in the designated solution, subjects waited at the site for 30 minutes for a visual acuity examination, slit lamp biomicroscopy and lens fit evaluation. Subjects were then allowed to leave the office with instructions to return 7 hours later. At 8 hours post lens insertion, subjects underwent CAC. The same allergy signs and symptoms evaluations done at Visit 4 were repeated at Visit 5.

Eighty subject were enrolled and 79 completed the evaluation. Each enrolled subject was randomly assigned to one of five treatment groups:

K-Lens 10 in one eye and a placebo lens in the fellow eye (N=30); or

K-Lens 25 in one eye and a placebo lens in the fellow eye (N=30); or

K-Lens 10 in both eyes (N=10); or

K-Lens 25 in both eyes (N=10)

Placebo lens in both eyes (N=10).

Primary Efficacy Measures

Three (3), five (5), and seven (7) minute post-challenge subject evaluation of ocular itching. Seven (7), fifteen (15), and twenty (20) minutes post challenge investigator evaluation of conjunctival redness. The results are presented in Table 1.

Secondary Efficacy Measures

Seven (7), fifteen (15), and twenty (20) minutes post challenge investigator evaluation of ciliary and episcleral redness, chemosis and mucous discharge and subject evaluation of lid swelling and tearing. The results are presented in Table 1.

TABLE 1

| Duration of Action (hours) | Post CAC Evaluation (min) | Mean Itching Score Difference* | |
|---|---|---|---|
| | | K-Lens 10 minus placebo | K-Lens 25 minus placebo |
| 12 | 3 | −0.6 | −1.1 |
| | 5 | −0.9 | −1.3 |
| | 7 | −0.9 | −1.2 |
| 8 | 3 | −0.8 | −1.1 |
| | 5 | −0.9 | −1.1 |
| | 7 | −0.9 | −1.1 |

*A clinically significant difference in the mean itching score is considered to be 1.0 unit or greater (K-Lens minus placebo). A negative value indicates that the eye wearing K-Lens experienced less severe itching as compared to the eye wearing the placebo lens.

TABLE 2

| Duration of Action (hours) | Post CAC Evaluation (min) | Mean Redness Score Difference | |
|---|---|---|---|
| | | K-10 minus placebo | K-25 minus placebo |
| 12 | 7 | −1.2 | −1.5 |
| | 15 | −0.7 | −1.0 |
| | 20 | −0.9 | −1.0 |
| 8 | 7 | −0.5 | −1.1 |
| | 15 | −0.7 | −0.1 |
| | 20 | −0.5 | 0.0 |

NOTE:
Since this is a composite score of redness (redness assessments were made at 3 different vessel beds), a greater than or equal to −3.0 unit mean score difference is required in 2 out of 3 time points to be considered clinically significant.

K-Lens 25 showed a clinically and statistically significant (>1.0 mean unit difference) inhibition of itching following the conjunctival allergen challenge.

The mean ocular itching score difference approached 1 unit for K-Lens 10 following the conjunctival allergen challenge.

Neither K-Lens 10 nor K-Lens 25 demonstrated a 1 unit or greater mean difference in ocular redness in any of the 3 different vessel beds.

Example 3

Release of Ketotifen from K-Lens 25

Figure 1:
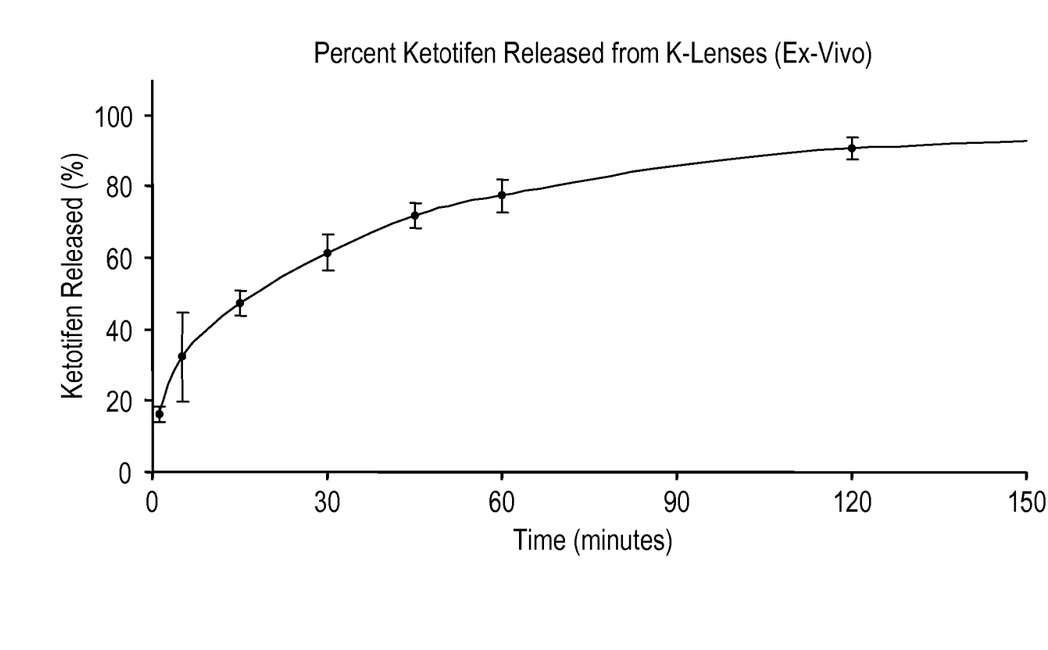
FIG. 1 illustrates the ex-vivo release of ketotifen.

K-Lens 25 were prepared as in Example 1 and the lenses were determined to contain about 19 µg of ketotifen per lens. The lenses were distributed to patients and worn by said patients for a period of time, as indicated by FIG. 1. Each lens was removed from the patient's eyes and blotted with lint-free blotting papers and transferred to a glass scintillation vial using tweezers. These lenses were stored in the closed glass vials in this state (dry state) until they were analyzed by the methods following below. Three milliliters (3 mL) of Eluent A (solution of 6.8 g, potassium phosphate, monobasic, 1653 mL deionized water, 340 mL acetonitrile, 2.6 mL o-phosphoric acid (85% aqueous)) were added to each vial. The vials were closed and sonicated for 1 hour at ambient conditions. The lenses were removed and 0.50 mL samples of the remaining lens extract were analyzed by HPLC (Agilent 1100 Series HPLC System, column: Agilent Zorbax Eclipse XDB-1 8, Rapid resolution HT 4.6 mm×50 mm×1.8µ, dector: wavelength: 299 nm, VW detector peak-width setting: >0.05 min, flow rate: 1.0 mL/min, needle wash solvent: Eluent B (solution of 6.8 g, potassium phosphate, monobasic, 994 mL deionized water, 1000 mL acetonitrile, 2.0 mL triethylamine, 2.6 mL o-phosphoric acid (85% aqueous), run time 25 min, injection volume 100 µL) The amount of ketotifen in any lens extract was determined by comparing the peak volume of the sample against a reference sample containing a known quantity of ketorifen. The percentage of ketotifen released from the lenses was calculated and that percentage was plotted versus the amount of time of lens wear. The results are shown in FIG. 1.

What is claimed is:

1. An ophthalmic device comprising a sterile etafilcon A contact lens sealed in a contact lens package said contact lens comprising a minimum effective amount of about 10 µg to about 25 µg of an anti-allergic agent selected from the group consisting of ketotifen, its pharmaceutically acceptable salts and mixtures thereof, wherein, the ophthalmic device is formed by adding the anti-allergic agent to a contact lens solution,
placing the contact lens in a contact lens package with said contact lens solution and anti-allergic agent,
sealing the contact lens package containing the contact lens, contact lens solution and anti-allergic agent; and
sterilizing the contact lens package,
wherein said contact lens releases between about 10% and about 90% of its contained anti-allergic agent between administering the contact lens to the eye and about 60 minutes.

2. The ophthalmic device of claim 1 wherein the anti-allergic agent is ketotifen fumarate.

3. The ophthalmic device of claim 1 wherein the anti-allergic agent is ketotifen fumarate.

4. The ophthalmic device of claim 1 wherein said ophthalmic device, anti-allergic agent and contact lens solution are sterilized at conditions from about 100° C. for about 8 hours to about 150° C. for about 0.5 minutes.

5. The ophthalmic device of claim 1 wherein said ophthalmic device, anti-allergic agent and contact lens solution are sterilized at conditions from about 115° C. for about 2.5 hours to about 130° C. for about 5.0 minutes.

6. The ophthalmic device of claim 1 wherein said ophthalmic device, anti-allergic agent and contact lens solution are sterilized at about 124° C. for about 18 minutes.

* * * * *

UNITED STATES PATENT AND TRADEMARK OFFICE
CERTIFICATE OF CORRECTION

PATENT NO. : 9,962,376 B2
APPLICATION NO. : 11/686979
DATED : May 8, 2018
INVENTOR(S) : Raja et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1199 days.

Signed and Sealed this
Second Day of July, 2019

Andrei Iancu
*Director of the United States Patent and Trademark Office*

UNITED STATES PATENT AND TRADEMARK OFFICE
CERTIFICATE OF CORRECTION

PATENT NO. : 9,962,376 B2
APPLICATION NO. : 11/686979
DATED : May 8, 2018
INVENTOR(S) : Ranganath R. Raja et al.

It is certified that error appears in the above-identified patent and that said Letters Patent is hereby corrected as shown below:

On the Title Page

Item [72] Inventor names are misspelled:
"Azaam Alti" should read --Azaam Alli--
"Brain Pall" should read --Brian Pall--

Signed and Sealed this
Fifth Day of March, 2024

Katherine Kelly Vidal
*Director of the United States Patent and Trademark Office*